United States Patent
Chen et al.

(10) Patent No.: US 9,693,512 B2
(45) Date of Patent: Jul. 4, 2017

(54) WIRELESS SENSOR SYSTEMS FOR HYDROPONICS

(71) Applicant: Aessense Technology Hong Kong Limited, Harbour, Kowloon (HK)

(72) Inventors: Tianshu Chen, Dublin, CA (US); Wenpeng Hsueh, San Ramon, CA (US); Huafang Zhou, San Jose, CA (US); Simon Wong, Los Altos, CA (US); Kent Kernahan, Cupertino, CA (US)

(73) Assignee: Aessense Technology Hong Kong Limited, Harbour, Kowloon (HK)

( * ) Notice: Subject to any disclaimer, the term of this patent is extended or adjusted under 35 U.S.C. 154(b) by 0 days.

(21) Appl. No.: 15/061,707

(22) Filed: Mar. 4, 2016

(65) Prior Publication Data
US 2016/0255781 A1    Sep. 8, 2016

Related U.S. Application Data

(63) Continuation-in-part of application No. 14/341,774, filed on Jul. 26, 2014, now abandoned.

(51) Int. Cl.
| | |
|---|---|
| *A01G 31/02* | (2006.01) |
| *H04W 4/00* | (2009.01) |
| *G01N 33/00* | (2006.01) |
| *H04W 84/18* | (2009.01) |
| *H04W 84/12* | (2009.01) |

(Continued)

(52) U.S. Cl.
CPC ......... *A01G 31/02* (2013.01); *G01N 33/0098* (2013.01); *G01N 33/18* (2013.01); *H04B 5/0037* (2013.01); *H04B 5/0081* (2013.01); *H04W 4/008* (2013.01); *H04B 5/0031* (2013.01); *H04W 84/12* (2013.01); *H04W 84/18* (2013.01)

(58) Field of Classification Search
CPC ........ A01G 31/02; A01G 31/00; A01G 31/06; Y02P 60/216; G05D 27/02; H04B 5/0031; H04W 4/008; H04W 84/12; H04W 84/18
See application file for complete search history.

(56) References Cited

U.S. PATENT DOCUMENTS

| | | |
|---|---|---|
| 6,619,835 B2 | 9/2003 | Kita |
| 2003/0102872 A1* | 6/2003 | Honda ................... G08C 17/00 324/438 |

(Continued)

FOREIGN PATENT DOCUMENTS

DK    WO 2009125023 A1 *  10/2009  ............... A01G 7/00

*Primary Examiner* — Devan Sandiford
(74) *Attorney, Agent, or Firm* — David Millers (57) ABSTRACT

A hydroponic system includes a first sensor system that measures one or more characteristics of a nutrient solution, a second sensor system that measures one or more characteristics of an environment of a plant; and a network device including a communication interface to the first sensor system and a communication interface to the second sensor system. The network device may be configured to transmit measurements from the sensor systems through a wireless network to a remote device or database. The network device and the sensor systems may be implemented in a housing that fits within a collar of the hydroponic system. The collar can allow easy replacement of the sensor systems and can electrically isolate the sensor systems.

18 Claims, 12 Drawing Sheets

(51) Int. Cl.
G01N 33/18 (2006.01)
H04B 5/00 (2006.01)

(56) References Cited

U.S. PATENT DOCUMENTS

| | | | | |
|---|---|---|---|---|
| 2005/0252078 | A1* | 11/2005 | Albright | A01G 7/02 47/58.1 LS |
| 2007/0273394 | A1* | 11/2007 | Tanner | A01G 25/167 324/664 |
| 2009/0025287 | A1* | 1/2009 | Lee | A01G 7/00 47/17 |
| 2009/0223128 | A1* | 9/2009 | Kuschak | A01G 31/00 47/62 N |
| 2010/0073669 | A1* | 3/2010 | Colvin, Jr. | G01J 3/02 356/218 |
| 2010/0199555 | A1* | 8/2010 | Pole | A01G 27/005 47/62 R |
| 2011/0031928 | A1 | 2/2011 | Soar | |
| 2012/0029709 | A1* | 2/2012 | Safreno | A01G 25/16 700/284 |
| 2013/0283689 | A1* | 10/2013 | Walliser | A01G 31/02 47/62 R |
| 2014/0106007 | A1* | 4/2014 | Shanahan | C02F 1/4674 424/661 |
| 2014/0144078 | A1* | 5/2014 | Gonyer | A01G 31/02 47/62 A |
| 2014/0177399 | A1 | 6/2014 | Teng et al. | |
| 2014/0182203 | A1* | 7/2014 | Church | A01G 31/02 47/62 N |
| 2014/0200690 | A1* | 7/2014 | Kumar | A01G 1/001 700/90 |
| 2014/0259920 | A1* | 9/2014 | Wilson | A01G 31/02 47/62 R |
| 2014/0273858 | A1 | 9/2014 | Panther et al. | |
| 2014/0275852 | A1 | 9/2014 | Hong et al. | |
| 2014/0275854 | A1 | 9/2014 | Venkatraman et al. | |
| 2014/0278220 | A1 | 9/2014 | Yuen | |
| 2015/0116117 | A1 | 4/2015 | Wisbey et al. | |
| 2015/0120202 | A1 | 4/2015 | Armstrong | |
| 2015/0120203 | A1 | 4/2015 | Wisbey et al. | |
| 2015/0135593 | A1* | 5/2015 | Ross | A01G 31/02 47/62 R |
| 2015/0190072 | A1 | 7/2015 | Armstrong | |
| 2015/0195009 | A1 | 7/2015 | Wang et al. | |
| 2015/0223418 | A1* | 8/2015 | Collins | A01G 31/02 47/62 R |
| 2015/0230735 | A1 | 8/2015 | Venkatraman et al. | |
| 2016/0000020 | A1* | 1/2016 | Sugimoto | G06Q 50/02 47/66.6 |
| 2016/0021836 | A1* | 1/2016 | Kernahan | H04L 67/10 700/284 |
| 2016/0021837 | A1* | 1/2016 | Kernahan | A01G 31/02 47/62 A |
| 2016/0024667 | A1* | 1/2016 | Shanahan | C25B 1/26 205/335 |
| 2016/0028442 | A1* | 1/2016 | Kernahan | H04B 5/0081 455/41.1 |
| 2016/0050862 | A1* | 2/2016 | Walliser | A01G 31/02 47/62 E |
| 2016/0128289 | A1* | 5/2016 | Wong | A01G 31/02 47/62 A |
| 2016/0135396 | A1* | 5/2016 | Day | A01G 31/02 700/275 |
| 2016/0143228 | A1* | 5/2016 | De Groot | A01G 9/24 700/284 |
| 2016/0178179 | A1* | 6/2016 | Hanson | A01G 1/00 362/249.02 |
| 2016/0219794 | A1* | 8/2016 | Greenberg | A01G 7/045 |
| 2016/0242372 | A1* | 8/2016 | Wong | A01G 31/02 |

* cited by examiner

WIRELESS SENSOR SYSTEMS FOR HYDROPONICS

CROSS-REFERENCE TO RELATED APPLICATIONS

This patent document is a continuation-in-part and claims benefit of the earlier filing date of U.S. patent application Ser. No. 14/341,774, filed Jul. 26, 2014, which is hereby incorporated by reference in its entirety.

BACKGROUND

Hydroponics allows growing of plants using nutrient aqueous solutions without soil, and aeroponics is a type of hydroponics that provides nutrient solutions in an aerosol of droplets that may be sprayed on or otherwise applied to plant roots. Hydroponic systems have been developed that include systems for delivery of a nutrient-rich solution to one or more plants, and such systems may be used outdoors, in a green house, or within a facility that provides a controlled environment for plant growth. Typically, such systems require significant and direct human monitoring and operations. In particular, a farmer may need to monitor plants growing in a hydroponic system, routinely adjust system settings, refill consumables, test the hydroponic system to be sure that the hydroponic system is operating properly, and repair or replace any faulty components. To be safe, frequent human intervention may necessary to avoid a failure that results in plants dying or growing poorly.

SUMMARY

In accordance with an aspect of the invention, a hydroponic system may include a control module able to connect to a cloud-based database to provide data regarding operation of in the hydroponic system or to accept control commands for control of the operation of the hydroponic system. In one configuration, a liquid sensing module of the hydroponic system may capture real-time data points such as measurements of solution temperature, pH, Electrical Conductivity (EC), Total Dissolved Solids (TDS), Dissolved Oxygen (DO), the presence or concentrations of specific chemicals or nutrients (e.g., nitrogen), Total Suspended Solids (TSS), and reservoir level for a nutrient solution and may provide the data points to the control module. Additionally, an air-sensing module may collect real-time data points such as measurements of atmospheric characteristics such as air temperature, air velocity or flow, relative humidity, and local atmospheric carbon dioxide ($CO_2$) and oxygen ($O_2$) concentrations and measurements of illumination characteristics such as the light intensity and spectrum. The control module may report the measurements from the liquid-sensing or air-sensing modules to the database and may execute control commands that depend on the measurements or the database. In particular, the control module may execute control commands to modify operation of the hydroponic system, e.g., to alter the nutrient solution or change lighting, temperature, or atmospheric concentrations around the plants, based on the measurements of the nutrient solution or the air environment.

One specific embodiment includes an interchangeable Water, Air, Network Device (WAND) containing one or more sensors. Different types of WANDs may contain different sets of sensors but may share a form factor that fits a hydroponic system. Having different types of WANDs with the same form factor allows a WAND in a hydroponic system to be easily removed and replaced to change the functionality of the hydroponic system, for example, when the plant being grown in the hydroponic system changes. In one configuration, the WAND may be devoid of internal power and instead may fit into a collar in a hydroponic system, where the collar induces power into the WAND. With standardized form factors for the WAND and collar, a hydroponic system may be repaired, altered, or upgraded by removing a WAND from the collar of the hydroponic system and inserting another WAND that fits into the collar but may have functionality that is the same or different from the functionality of the removed WAND.

Another specific embodiment is a hydroponic system that includes a plant fixture, a reservoir, a water or reservoir sensor system, an open-air sensor system, and a network device. The reservoir configured to contain a nutrient solution for growing of a plant in the plant fixture, and the reservoir sensor system measures one or more characteristics of the nutrient solution. The open-air sensor system measures one or more characteristics of an environment surrounding the plant. The network device may include a communication interface to the reservoir sensor system and a communication interface to the open-air sensor system, and the network device may be configured to transmit measurements from the sensor systems through a wireless network to a remote device or database.

BRIEF DESCRIPTION OF THE DRAWINGS

The drawings illustrate examples for the purpose of explanation and are not of the invention itself. Use of the same reference symbols in different figures indicates similar or identical items.

DETAILED DESCRIPTION

Various implementations are described in detail herein with reference to the accompanying drawings, but references made to particular examples or implementations are for illustrative purposes and are not intended to limit the scope of the invention or the claims.

Some implementations of hydroponic systems disclosed herein use a network device, sometimes referred to herein as a Water, Air, Network Device or WAND, which may be placed in a collar in the hydroponic system. The variety of devices available for implementations of a WAND and a collar make it impractical to describe all possibilities in a disclosure. A WAND system may, for example, include many sensors, one sensor, or even no sensors within the scope of the present disclosure. Absent any sensors a WAND may be useful as a control or communications device, for example, as an access point, repeater, gateway, or bridge between two different communications technologies.

By way of example, a WAND for providing sensor and communications for an aeroponic growth system is presented. One of ordinary skill in the related arts will appreciate the generality of the disclosure and know how different implementations may be designed. All such are within the scope of this disclosure and claims.

Figure 1:
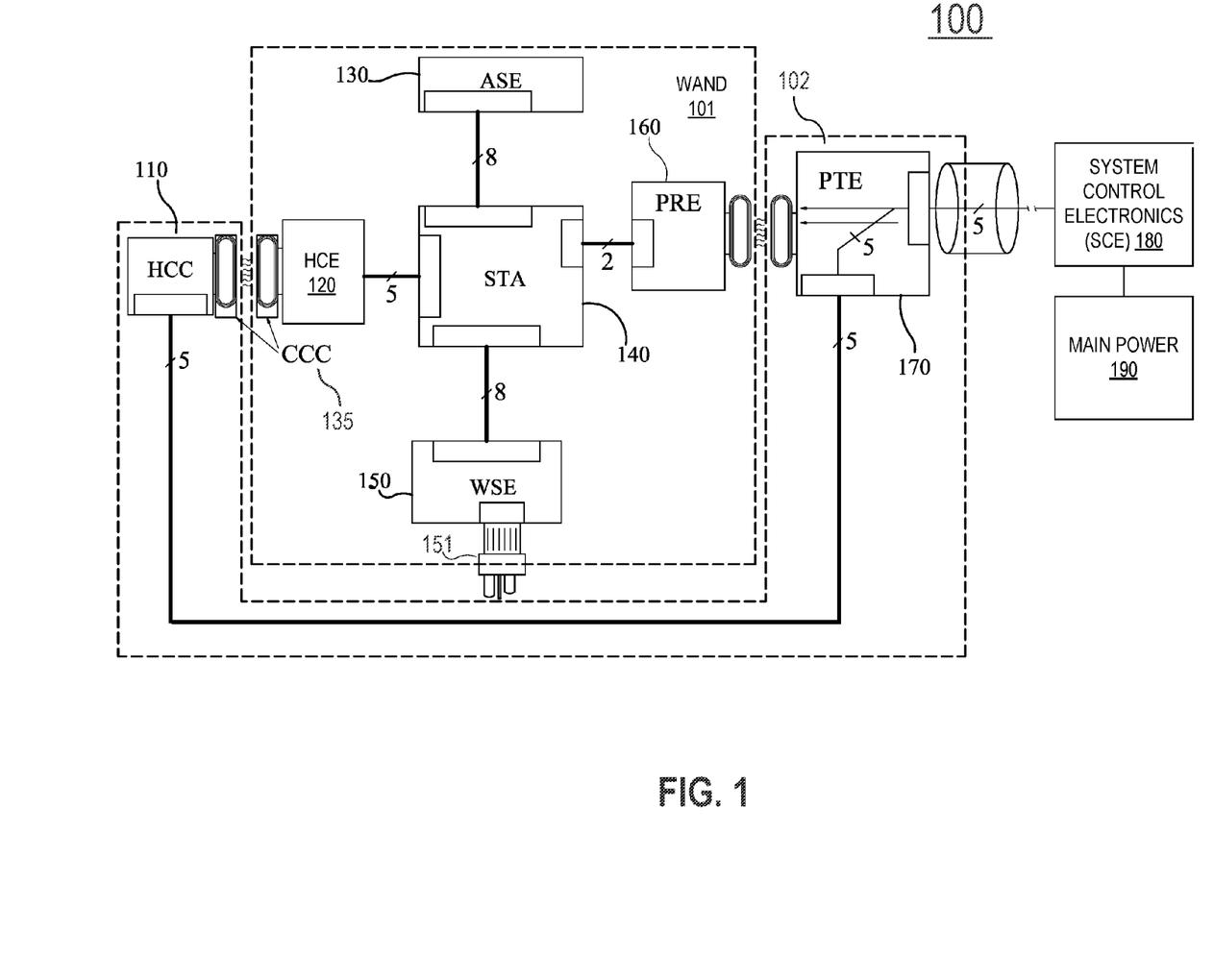
FIG. 1 is a top level schematic showing subsystems of an exemplary system may be electrically connected.

Looking to FIG. 1, an exemplary WAND and collar system 100 includes a WAND 101 and a collar 102, customized for an exemplary aeroponic growth system. WAND 101 includes H-Field Communications Electronics (HCE) 120, Air Sensor Electronics (ASE) 130, a Station Board (STA) 140, Water Sensor Electronics (WSE) 150, and Power Receiver Electronics (PRE) 160. Collar 102 includes an H-Field Communications Collar (HCC) 110 and Power Transmitter Electronics (PTE) 170. In the example of FIG. 1, PTE 170 employs power, ground, and data lines connected to System Control Electronics (SCE) 180 and a main power supply 190. SCE 180 may control a hydroponic (or aeroponic) system that provides an environment in which plants grow. Main power supply 190 may be or connect to a line voltage from a power company and may be transformed or rectified in different ways to power SCE 180 and other subsystems or the hydroponic system. Accordingly, SCE 180 and main power supply 190 are not strictly speaking a part of collar 102 but may connect to WAND 101, for example, to communicate information through with or through WAND and collar system 100.

The major example blocks are described in detail. In some instances, component part numbers may be stated.

Figure 2:
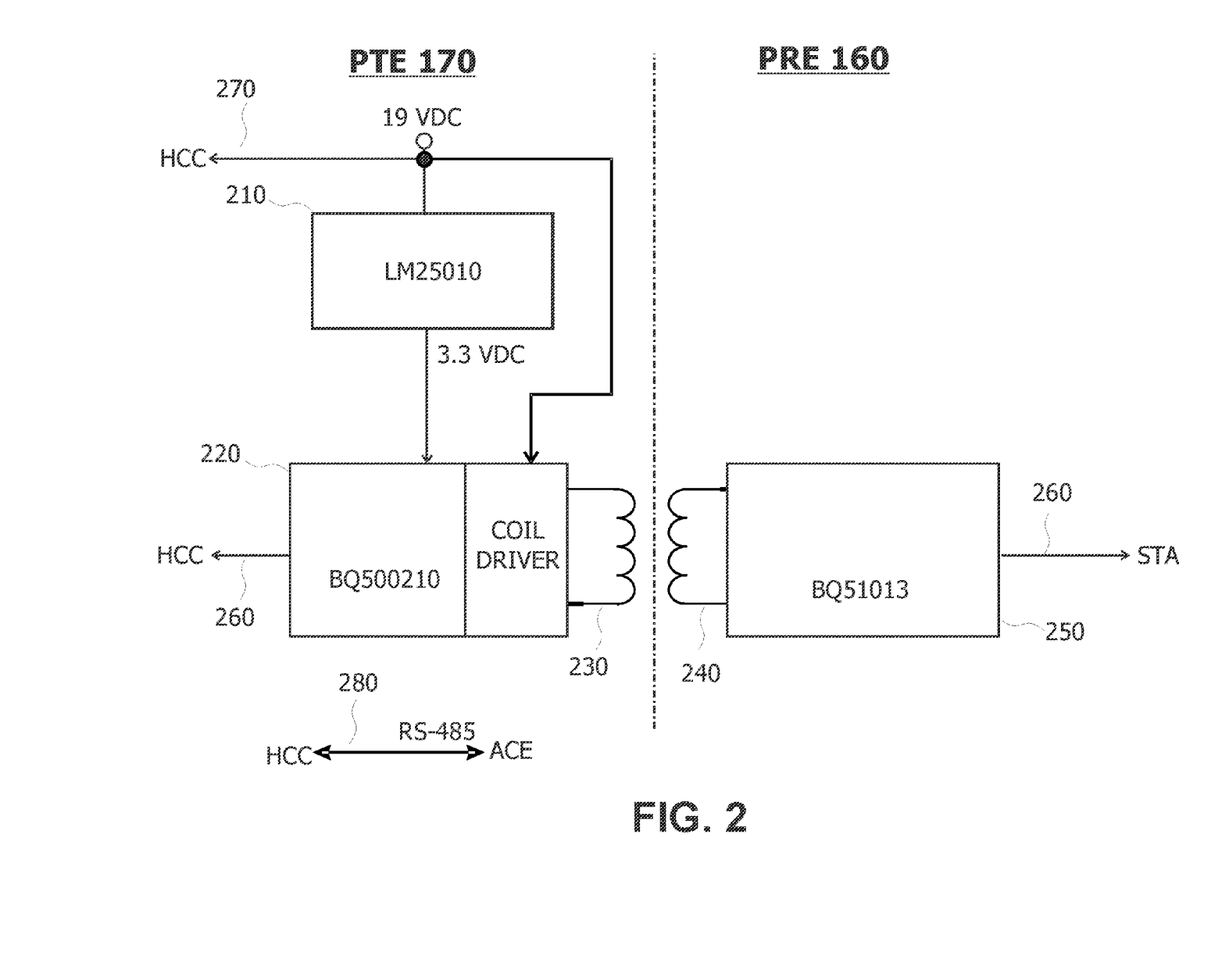
FIG. 2 shows an exemplary wireless power system.

PTE 170 may be implemented in a variety of ways. PTE 170 in an exemplary implementation provides power to PRE 160, which may be inside a housing of WAND 101, and PRE 160 distributes power within WAND 101 to HCE 120, ASE 130, STA 140, and WSE 150. FIG. 2 shows PTE 170 coupled to PRE 160 for power transfer from the collar to the WAND. In the illustrated configuration of PTE 170, a regulator 210 such as an LM25010 regulator receives 19 VDC from an external supply. Regulator 210 provides a 3.3 VDC output, which powers a manager 220 such as a Texas Instruments P/N BQ500210 "Qi Compliant Wireless Power Transmitter Manager" 220. Manager 220 provides a pulse width modulation (PWM) drive signal to a high speed coil driver, for example a Texas Instruments TPS28225, which in turn drives a transmitting coil 230, e.g., a Wurth Wireless Power Charging Transmitter Coil 230 P/N 760368110 using the 19-VDC supply. When the WAND is placed in the collar for use, transmitting coil 230 is proximate to a receiving coil 240 such as a TDK P/N WR-483250, which is electrically connected to a Texas Instruments BQ51013 Wireless Power Receiver 250 in PRE 160. The 5.0 VDC output of the power receiver 250 may be provided to STA 140 on a line 260.

Figure 3:
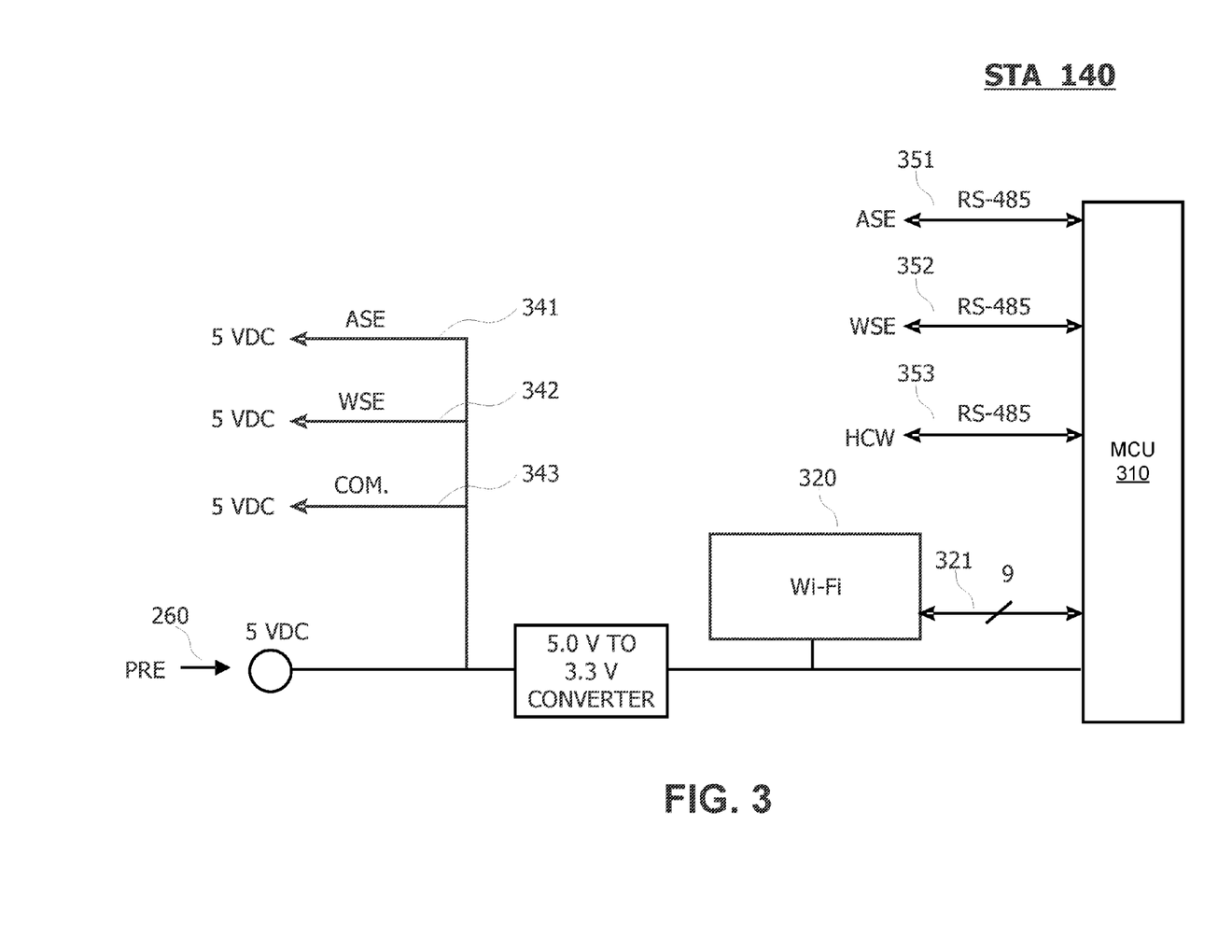
FIG. 3 shows an electronic subsystem including Wi-Fi capability.

Looking to FIG. 3, 5.0-VDC power received by STA 140 from PRE 160 on line 260 is further provided directly to the HCE 120 on a line 343, WSE 150 on a line 342, and ASE 130 on a line 341. 5.0 VDC power is converted to 3.3 VDC and provided to a Wi-Fi unit 320, for example a Microchip MRF24WG0MA. Wi-Fi unit 320 responds to data and commands provided by a microcontroller unit (MCU) 310, for example a Microchip PIC32MX695F512L via a nine-line bus 321. STA 140 may also include RS-485 communications capability between MCU 310 and ASE 130 on a bus 351, WSE 150 on a line 352, and HCE 120 on a line 353.

Figure 4:
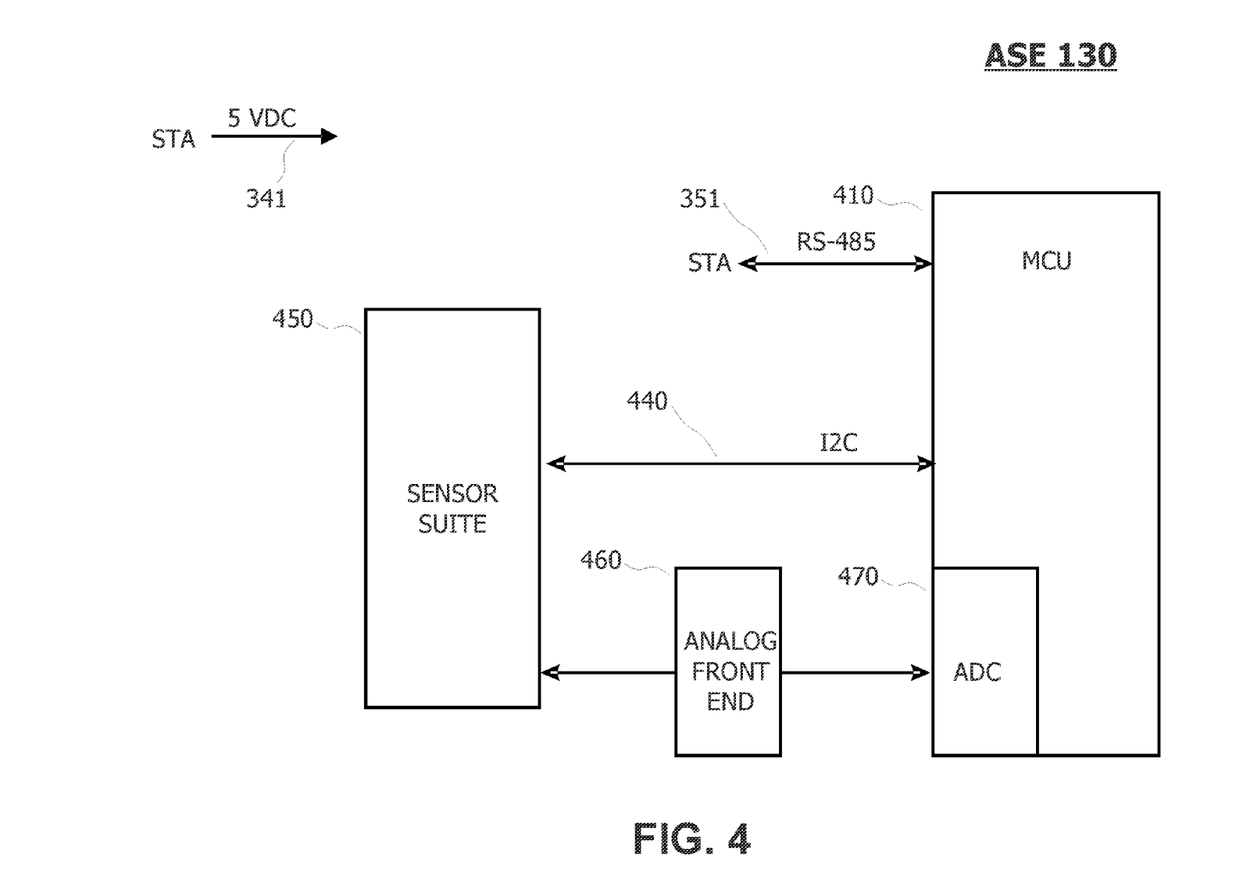
FIG. 4 shows an open-air sensor subsystem.

STA 140 may connect to ASE 130, which may support a suite of sensors for sensing characteristics of the environment of a growing plant. In addition to power and ground on line 341, STA 140 may have an RS-484 communications for wire, two-way communication with ASE 130 via bus 351. ASE 130 may include a suite of environmental sensors 450 as shown in FIG. 4. Examples of environmental sensors 450 include sensors that measure concentrations of $CO_2$, CO, and $O_2$ in the atmosphere around a plant and sensors that measure characteristics of the ambient light in the environment. Some embodiments of ASE 130 may include an MCU 410, for example, a PIC32MX350F256H microcontroller, wherein MCU 410 includes an analog-to-digital converter (ADC) 470 as shown in FIG. 4. Some embodiments of ASE 130 include a multiplexer (MUX) or analog front end 460 for selecting analog measurement signals from sensor suite 450. Some MCUs 410 may have enough analog input pins, so that an external MUX 460 is not required. MCU 410 may manage the sensors, for example powering them up or down, placing one or more sensors in standby or operative mode, determining the status of one or more sensors, or performing diagnostics on one or more sensors. MCU 410 may also be programmed to receive requests for data related to a given sensor and to provide the data back to STA board 140 via the RS-485 bus 420. STA 140 may then provide the data to the requester via the Wi-Fi unit 320 or another data link.

Figure 5:
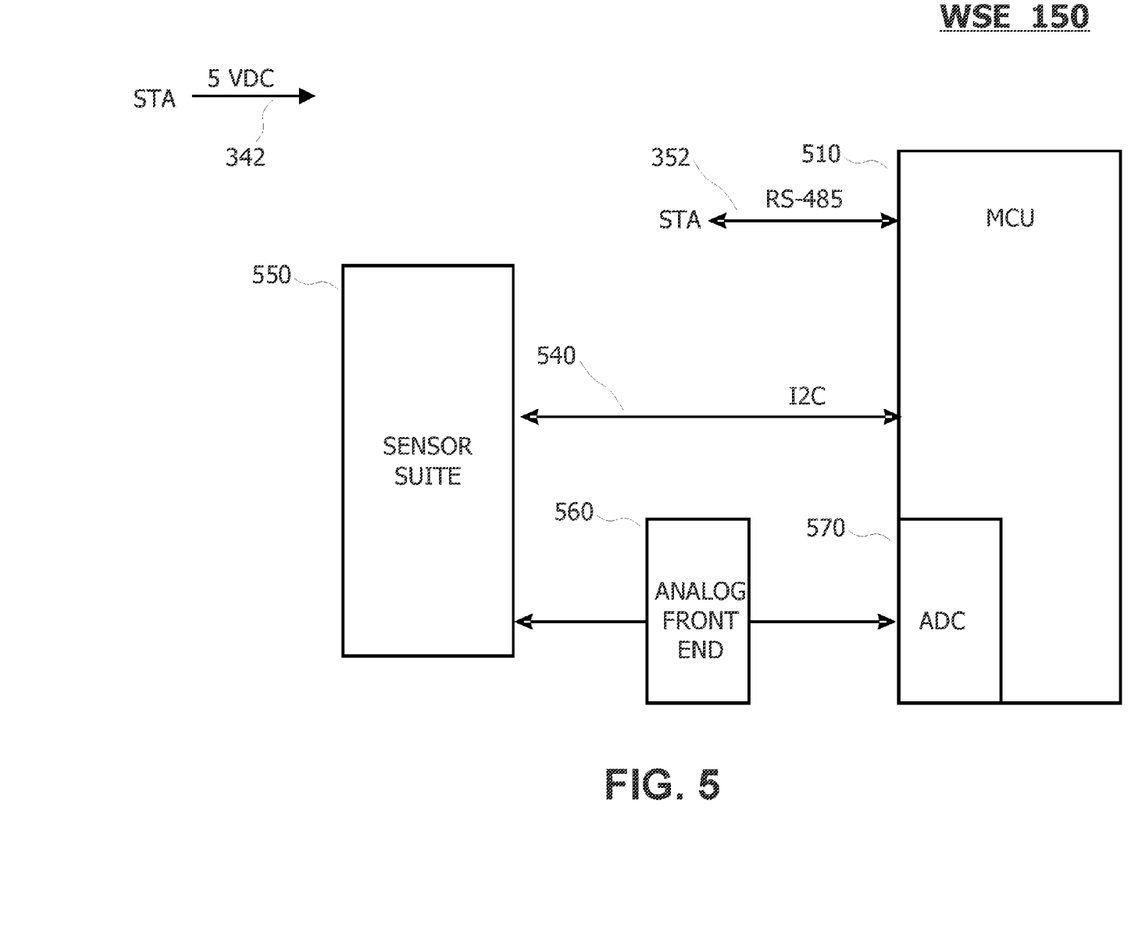
FIG. 5 shows a reservoir or water sensor subsystem.

WSE 150 may be similar to the ASE 130. WSE 150 may receive DC power from STA 140 on line 342 and may also send and receive data on an RS-485 wired communications bus 352. In the example shown in FIG. 5, WSE 150 includes a suite of water sensors 550, and the sensors 550 may be submerged in a water medium. Examples of sensors 550 include any c combination of pH sensors, temperature sensors, total dissolved solids (TDS) sensors, sensors of specific chemicals, resistivity sensors, and any other sensors useful for sensing one or more characteristics a nutrient solution in a hydroponic system. In the illustrated embodiment, WSE 150 includes an MCU 510, for example, a PIC32MX350F256H microcontroller, wherein MCU 510 includes an analog-to-digital converter (ADC) 570. Some embodiments of WSE 150 include a MUX or analog front end 560 to increase the number of sensors in sensor suite 550 able to provide measurements to MCU 510. Some MCUs 510 may have enough analog input pins so that an external MUX 560 is not required. MCU 510 may manage the sensors in sensor suite 550, for example, powering one or more sensors up or down, placing one or more sensors in standby or operative mode, determining the status of any sensor, and/or performing diagnostics processes on any of the sensors. MCU 510 may also be programmed to receive requests for data related to a given sensor and to provide the data back to STA board 140 via the RS-485 bus 520. STA 140 may then provide the data to the requester via the Wi-Fi unit 320 or another data link.

Figure 6:
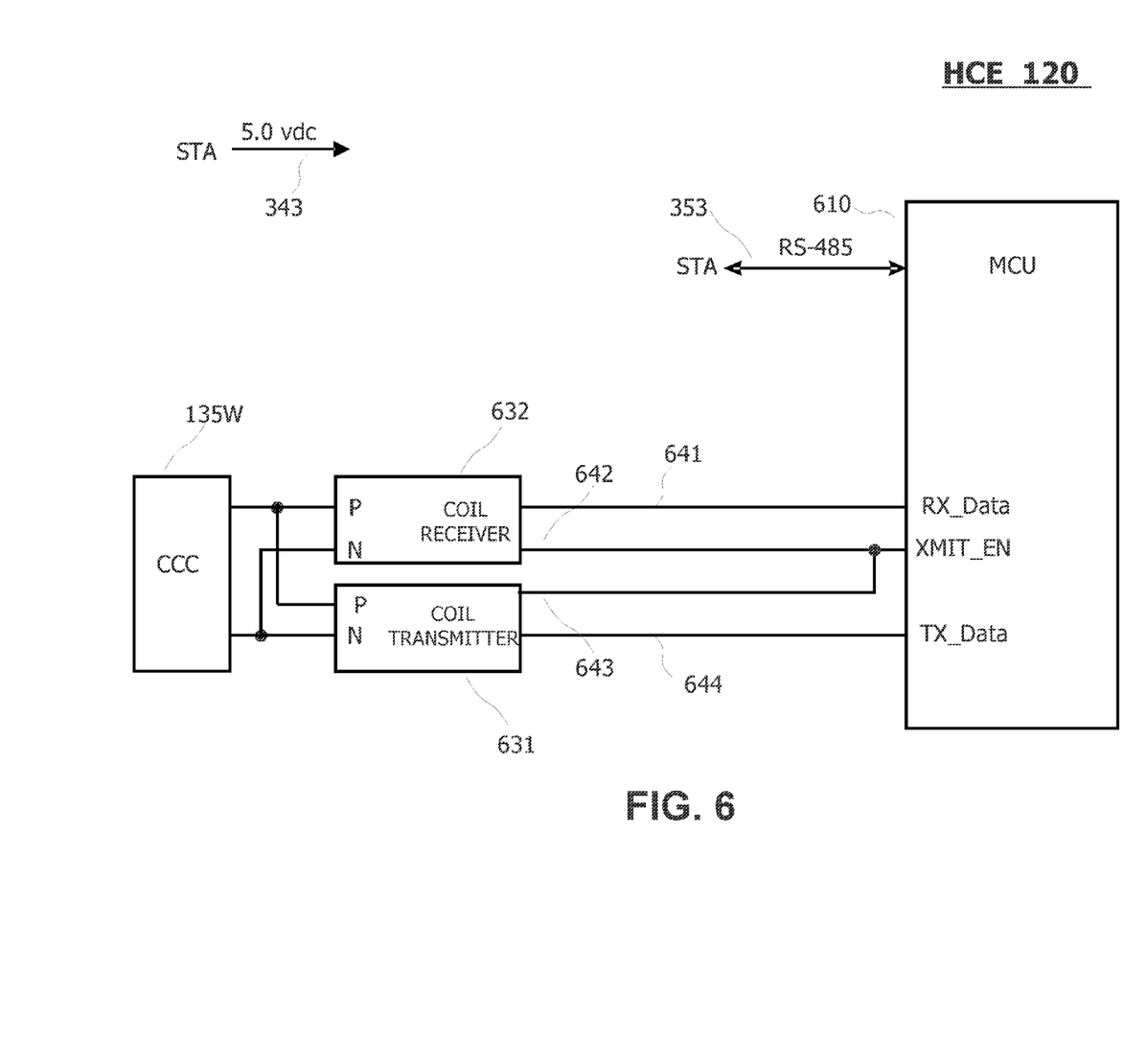
FIG. 6 shows an H-field local communications subsystem for an electrically isolated device.

Looking to FIG. 6, HCE 120 and HCC 110 operate in a similar fashion to PTE 170 and PRE 160, except data is exchanged between the transmitting and receiving coil rather than power. HCE 120 receives 5.0 VDC power from STA on the line 343. An MCU 610, for example, a Microchip PIC32MX350F128D, may communicate with STA 140 via the RS-485 bus 353. In the implementation shown in FIG. 6, MCU 610 receives data on a line 641 and sends data on a line 644. Data activity is controlled by an enable signal XMIT_EN on a line 642, 643. The signals connect MCU 610 to a coil transmitter 631 and a coil receiver 632. The P and N signals from the coil transmitter 631 and the coil receiver, connected as shown, to drive a coil, e.g., a CCC 135W coil. CCC 135W coil interacts with a matching (may be identical) coil CCC 135C on HCC 110, the pair of coils being proximate to enable inductively passing data signals when the WAND is inserted for operation. An example of the CCC 135 coil is a TDK WR-483250-15M2-G.

Figure 7:
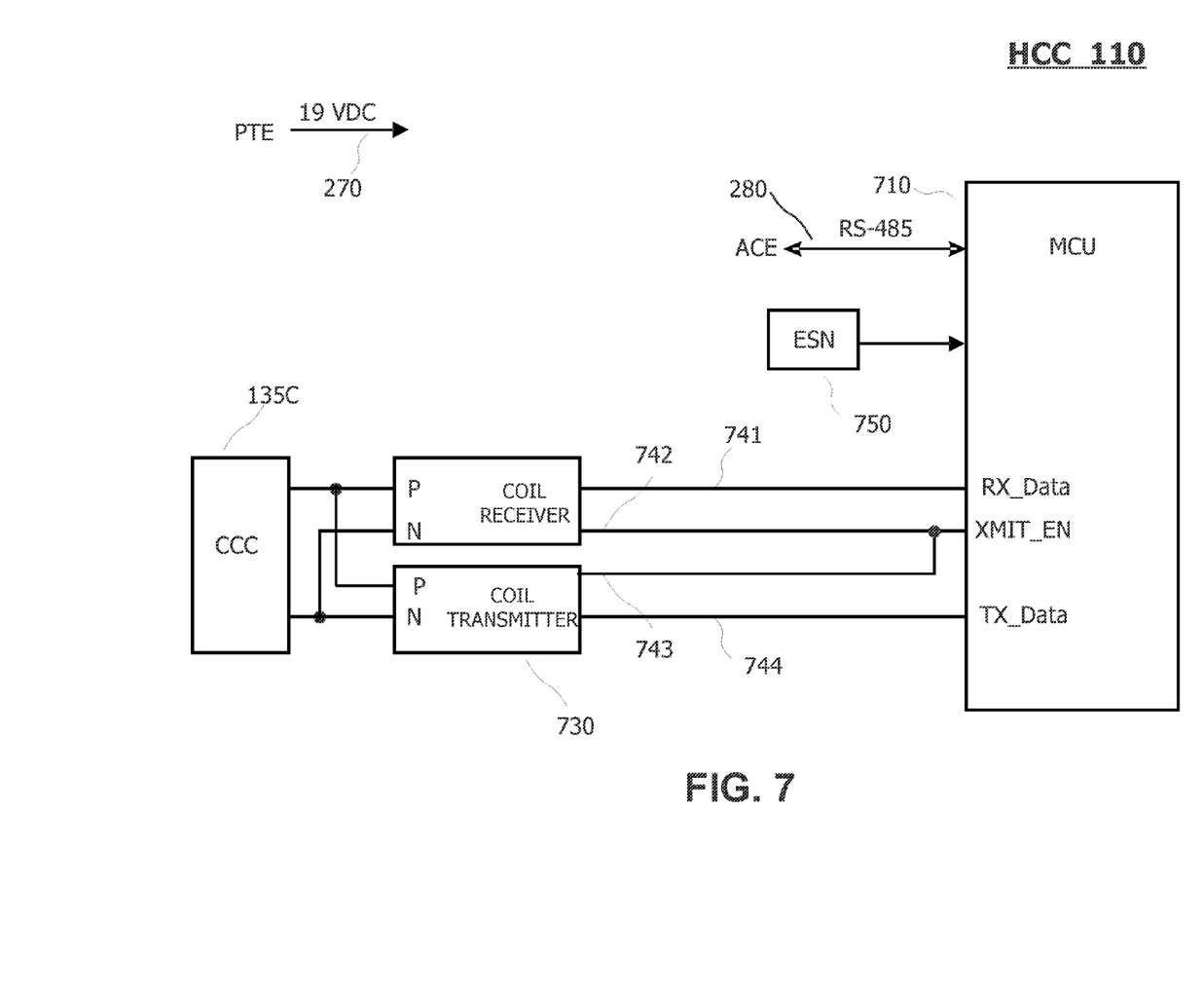
FIG. 7 is an H-field communications system used in a collar for an electrically isolated device.

Looking now to FIG. 7, HCC 110 receives 19 VDC power on a line 270 from the PTE 170. Except for operating voltage, HCE 120 and HCC 110 are very similar in operation.

An MCU 710, for example, a Microchip PIC32MX350F128D, may communicate with SCE 180 via the RS-485 bus 280, which may be a pass-through in PTE 170. In the embodiment of FIG. 7, MCU 710 receives data on a line 741 and sends data on a line 744. Data activity is controlled by enable signal XMIT_EN on a line 742, 743. The signals connect MCU 710 to a coil transmitter 731 and a coil receiver 732. The P and N signals from the coil transmitter 731 and the coil receiver, connected as shown, drive a CCC 135C.

HCC 110 includes an ESN (electronic serial number) 750, for example a Maxim Integrated DS2411. WAND and collar system 100 may be used to provide sensors and communications capability to a fixed piece of equipment. A given the technology incorporated in WAND 101, such as the content of sensor suites 450 and 550, may be known or determined from a manufacturer's product model number. As such, all WANDs 101 bearing the same model number may be expected to be the same. That is, the WANDs would be freely interchangeable. However the fixed equipment may be one of an unlimited number of otherwise identical units, and a supervisory system would need to know from which fixed piece of equipment data is being sent to or received from a WAND 101. The number in an ESN is deemed to be unique, and known to the supervisory system. In some embodiments WAND 101 may be paired to a certain piece of fixed equipment by interrogating HCC 110 through the CCC 135 communications link and asking MCU 710 to report the serial number stored in its ESN 750.

As mentioned hereinbefore, there may be electronics in the equipment including the collar 102. By way of example, SCE 180 can control an aeroponic growth system. SCE 180 may be designed to make use of water sensors in WSE 150 or environmental sensors in ASE 130. In addition, WAND 101 may provide communications capability via the Wi-Fi instantiated within STA 140 subsystem of WAND 101. The communications may be for the purpose of providing data to an external system or receiving commands from an external system. One of ordinary skill in the art will know of many other purposes, depending upon the fixed equipment and its purpose.

Figure 8:
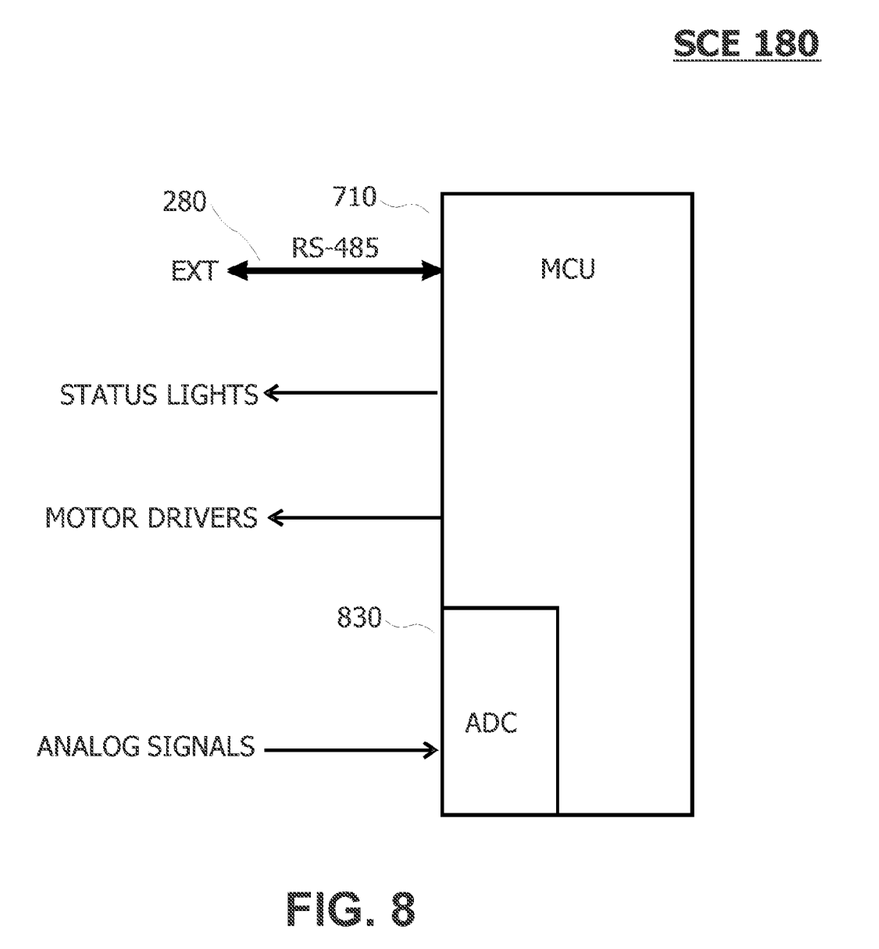
FIG. 8 shows an example of system control electronics for a hydroponic system.

Per FIG. 8, an SCE 180 may communicate with WAND 101 via HCC 110 on an RS-485 bus 280. SCE 180 may include an MCU 810, which includes a number of general purpose input/output (GPIO) pins 820. Some systems may include an ADC 830 to provide a digital version of analog signals connected to the ADC 830. In an aeroponic system, MCU 810 may provide signals to turn fans ON or OFF, as well as motor drivers, relays, and the like. In one embodiment, SCE 180 includes a variety of colored lights, wherein MCU 810 may turn on a light of an appropriate color, for example green, yellow, or red and optionally a noise-producing device to provide a quick and easy status value to an observer. In some embodiments, SCE 180, likely being connected to grid power, which provides the 19-VDC supply voltage to PTE 170.

Figure 9:
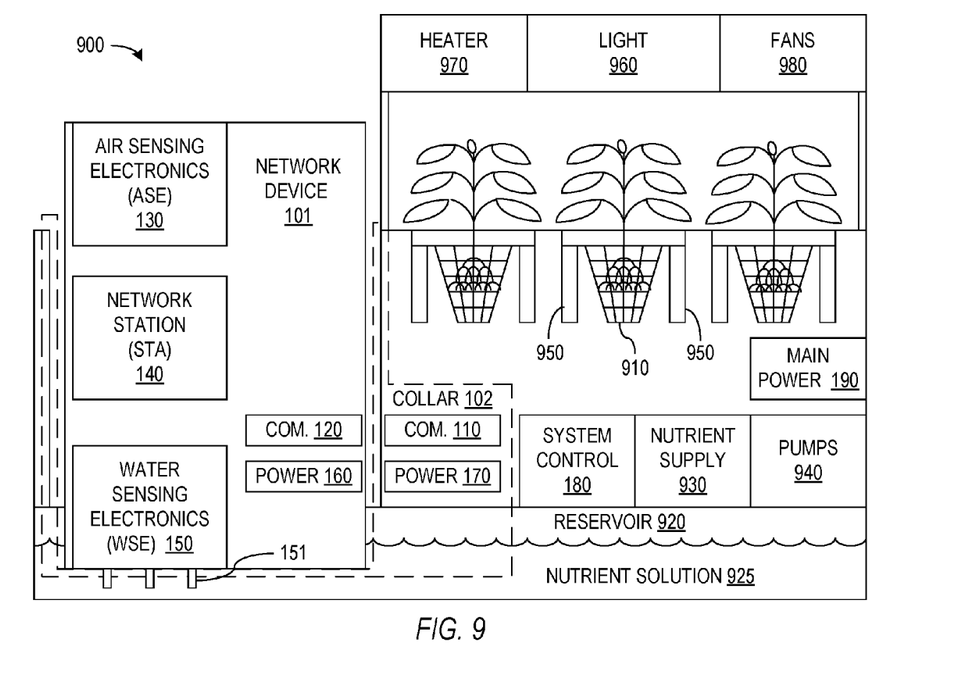
FIG. 9 is a block diagram of a hydroponic system employing an inductive coupling to power and communicate with sensor systems and a network device.

FIG. 9 is a block diagram of a hydroponic growth system 900 including a network device 101 similar or identical to WAND 101 described above. In the illustrated embodiment, hydroponic growth system 900 is an aeroponic growth system that includes plant fixtures 910 that hold growing plants and includes a reservoir 920 containing a nutrient solution 925. Hydroponic system 900 further includes subsystems that provide for the needs of growing plants. For example, a nutrient supply 930 may supply a variety of different nutrients that may be mixed with water to provide nutrient solution 925 with a composition suited for the plants being grown. Pumps 940 can mix nutrient solution 925 and provide solution 925 to misters 950 that spray or otherwise apply nutrient solution 925 to the roots of plants in fixtures 910. A lighting system 960 can provide illumination for photosynthesis and plant growth, and systems such as a heater 960 and fans 970 may be able to manipulate the humidity, composition, temperature, and flow or velocity of the air around the growing plants. In some implementations, system control electronics 180 may be programmed to determine operating parameters of hydroponic subsystems 930, 940, 950, 960, 970, and 980 based on measurements, data, or instructions from ASE 130, WSE 150, or a remote device communicating through network station 140.

As illustrated, network device 101, which includes ASE 130, network station 140, and WSE 150 enclosed in a shared housing, fits into collar 102 of hydroponic system 900. Network device 101 and collar 102 may have matching shapes or form factors such that when network device 101 is inserted into collar 102, H-field communications electronics 110 and 120 in collar 102 and device 101 are aligned for an inductive coupling and electronics 101 and 120 can decode induced voltages to decipher communicated information. Similarly, power transmitter electronics 170 and power receiver electronics 160 are aligned to create an inductive coupling for power transmission when network device 101 is properly inserted in collar 102. The inductive coupling of systems 110 and 120 for data communications between network device 101 and system control electronics 180 and the inductive coupling of systems 160 and 170 for supplying power to network device 101 may make hydroponic system 900 safer and less vulnerable to electrical shorts. In particular, a portion 151 of water sensing electronics 150 may need to be in nutrient solution 925, and inductive couplings may isolate a direct short to nutrient solution 925 from main power supply 190 and make such shorts less hazardous to human users and less damaging to electronics components.

The inserting network device 101 in collar 102 may automatically position a portion 151 of water sensing electronics 150 in nutrient solution 925, so that water sensing electronics 150 can sense or measure characteristics of nutrient solution 925. Inserting network device 101 in collar 102 may similarly position a portion of air sensing electronics 130 for sensing or measuring characteristics of the environment around the plants growing in hydroponic system 900 or for measuring characteristics of the plants. In general, the sensors provided in a particular implementation of network device 101 may be selected for the type of plants being grown in hydroponic system 900 or alternatively may be general purpose sensors useful when growing a variety of different plants. Some examples sensors that may be included in air sensing electronics 130 include a light intensity sensor, a spectrometer or other sensor for measuring the spectral content of light, a temperature sensor, an air flow or air velocity sensor, a humidity sensor, an oxygen sensor, a carbon dioxide sensor, a carbon monoxide sensor, and sensors or other airborne chemicals or particulates. Some examples sensors that may be included in water sensing electronics 150 include a reservoir level sensor, a pH sensor, an electrical conductivity sensor, a total dissolved solids sensor, dissolved oxygen, a total suspended solids, and sensors of other specific chemicals or nutrients. FIG. 9 illustrates one example in which network device 101 is easily removable, so that sensor suites in network device 101 can be easily swapped by changing network device 101, for example, when hydroponic system 900 is switched to growing a different type of plant. In particular, a variety of different types of network devices 101 having different sensor combinations may have housings with a form factor or shape that matches the form factor or shape of collar 102.

Figure 10:
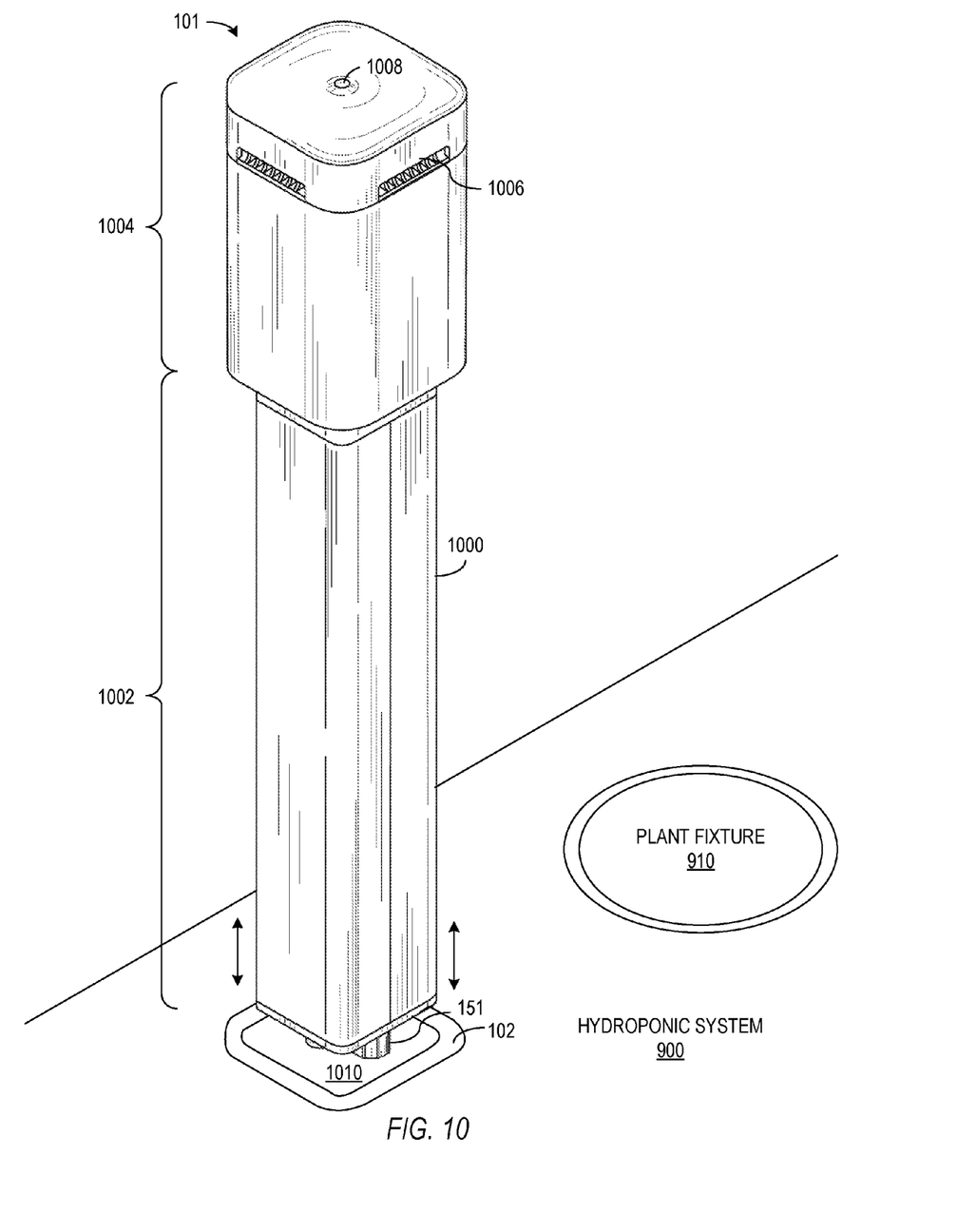
FIG. 10 illustrates how an electrically isolated sensor and network device may be inserted or removed from a collar in a hydroponic system.

FIG. 10 illustrates how a network device 101 may be inserted or removed from a collar 102 of a hydroponic system 900. As illustrated, network device 101 has a housing 1000 with a lower portion 1002 shaped to slide into and fit snuggly within an opening or guide tube 1010 of collar 102. Guide tube 1010 and the lower portion 1002 of housing 1000 have matching or keyed cross-sections, which may be asymmetric so that network device 101 can only be inserted into guide tube 1010 with a desired orientation. For example, guide tube 1010 and lower portion 1002 may have a generally square or rectangular shape with one corner being rounded or clipped differently from the other corners. The length of lower portion 1002 may also be chosen so that a portion 151 of the water sensing electronics in network device 101, which may extend from the bottom of housing 1000, is in the reservoir of hydroponic system 900 and is submerged in the nutrient solution when network device 101 is fully inserted in collar 102. Housing 1000 further includes a upper portion 1004 that may remain above a top surface of hydroponic system 900, so that air vents 1006 and an optical system 1008 for sensors in the air sensing electronics of network device 101 may better sense the environment around plants in a fixtures 910 of hydroponic system 900.

Figure 11:
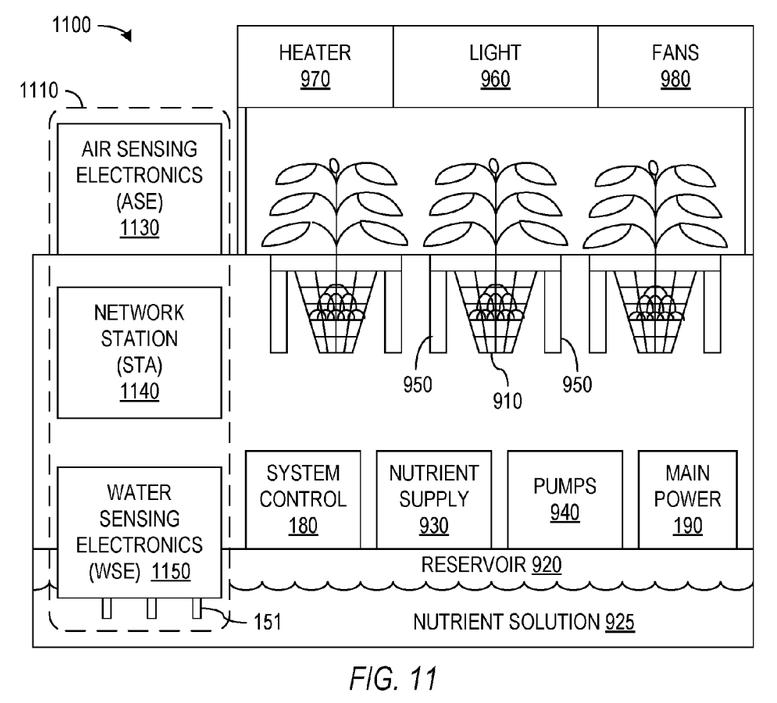
FIG. 11 is a block diagram of a hydroponic system employing separate modules for air sensor electronics, water sensor electronics, and a network station.

FIG. 11 shows a hydroponic system 1100 according to an alternative implementation of an air sensing electronics (ASE) module 1130, a network station 1140, and a water sensing electronics (WSE) module 1150. In the implementation of FIG. 11, air sensing electronics module 1130, network station 1140, and water sensing electronics module 1150 may be separate modules of hydroponic system 1100, rather than being components in the housing of a removable WAND. For example, each module 1130, 1140, and 1150 may be implemented on separate circuit boards, and the circuit boards may be interconnected with wires or cables or may communicate with each other wirelessly. Using separate modules may provide greater design freedom for positioning of air and water sensors, e.g., air sensing electronics module 1130 may be above plants while water sensing electronics module is adjacent to or in reservoir 920. Air sensing electronics module 1130, network station 1140, and water sensing electronics module 1150 may otherwise function in the same manner as described above for ASE 130, network station 140, and WSE 150. Hydroponic system 1100 further includes subsystems such as plant fixtures 910, nutrient solution reservoir 920, nutrient supply 930, pumps 940, misters 950, lights 960, a heater 970, and fans 980 that operate under the control of control electronics 180 to provide for the needs of growing plants as described above with reference to FIG. 9.

STA module 1140 provides network communications for connecting wirelessly to remote network devices or a cloud-based database, for example, for backing up plant growth data or data points such as measurements that ASE module 1130, WSE module 1150, or other sensors or systems in hydroponic system 1100 acquire. STA module 1140 can also accept control commands for operation of hydroponic system 1100 and provide the commands to system control electronics 180. In an exemplary implementation, STA module 1140 uses RS-485 bus protocols and interfaces for communication with two sensing modules, WSE module 1150 and ASE module 1130, but alternatively STA module 1140 may connect wirelessly to ASE module 1130 or WSE module 1150.

Water sensing electronics module 1150 collects aqueous based data points such as real time measurements of temperature, pH, Electrical Conductivity (EC), Total Dissolved Solids (TDS), Total Suspended Solids (TSS), Dissolved Oxygen (DO), and reservoir level of nutrient solution 925 in reservoir 920. In one configuration, water sensing electronics module 1150 interfaces with STA module 1140 via RS-485 bus, instead of using an H-field or inductive communication coupling, and STA module 1140 may powered from main power supply 190 of hydroponic system 1100. Alternatively, WSE module 1150 may connect to STA 1140 wirelessly, and WSE module 1150 may be isolated from many power 190 and operate on battery power or inductive power couplings such as provided by power receiver electronics 160 and power transmitter electronics 170, which are described above.

Air sensing electronics module 1130 collects open-air based data points such as real time measurements of air temperature, relative humidity, carbon dioxide ($CO_2$) and oxygen ($O_2$) levels, and illumination characteristics such as brightness and spectral distribution. ASE module 1130 may interface to STA module via a wired connection such as an RS-485 bus. ASE module 1130 may alternatively run on battery power or may connect to STA module 1140 wirelessly. Although ASE module 1130 may have less shorting risk than does WSE module 1150, local wireless communications such as a Bluetooth communications may facilitate locating ASE module 1130 remotely from STA module 1140 or WSE module 1150. For example, ASE module 1130 may be located in a portion of hydroponic system 1100 that is above the plants, while WSE module may be in reservoir 920 and STA module 1140 may be adjacent to system control electronics 180.

Figure 12:
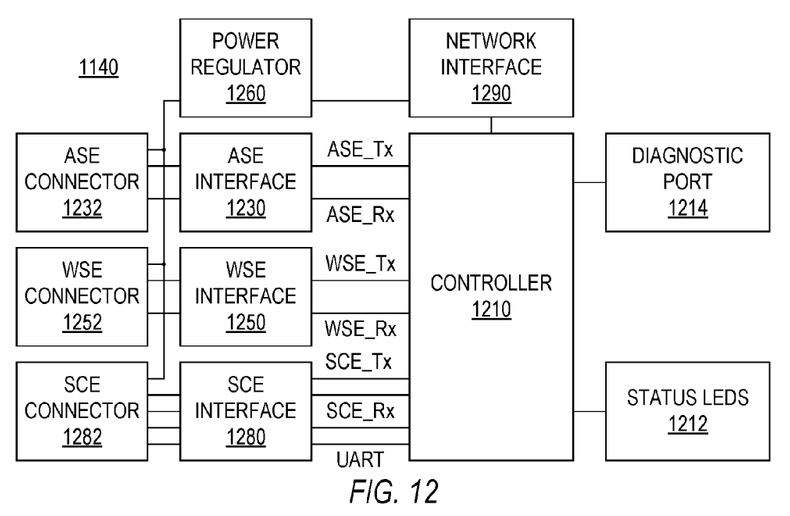
FIG. 12 is a block diagram of an implementation of a network station module.

FIG. 12 is a block diagram of one implementation of network station module 1140. In the illustrated implementation, network station module 110 includes a microcontroller 1210 that may be programmed for desired communications among sensor modules 1130 and 1150, system control 180, and through a network to a remote device. For example, controller 1210 may execute software or firmware to collect data points from ASE module 1130, WSE module 1150, or system control electronics 180, to upload the data points to a remote device or cloud database, and to provide system control electronics 180 with the data points or with data, commands, or instructions received from a wireless network. In the illustrated implementation, controller 1210 has status lights 1214, e.g., red, yellow, and green status LEDs, through which controller 1210 can indicate the status of network station 1140 and has a diagnostic port 1212 for testing operation of network station 1140.

Controller 1210 connects to an ASE interface 1230, which may be a chip or other electrical circuit that implements a signaling protocol to transmit or receive communications with ASE module 1130. For wired communication, ASE interface 1230 may be RS-485 compliant and may connect to ASE module 1130 through a connector 1232, e.g., an RJ-45 connector, and a cable not shown. Similarly, controller 120 connects to WSE interface 1250 and SCE interface 1280, which respectively allow wired communication with WSE module 1150 and system control electronics 180 through respective connectors 1252 and 1282 and cables not shown. For wired connections, a power regulator 1260, which provides power to controller 1210 can also provide power or receive power via connectors 1232, 1252, and 1282 to ASE module 1130, WSE module 1250, and system control electronics 180. Alternatively, one or more of interfaces 1230, 1250, and 1280 may implement a local wireless communication protocol, e.g., Bluetooth, that enables network station 1140 to communicate wirelessly with ASE module 1130, WSE module 1250, or system control electronics 180.

A network communication interface 1290 may be a chip or electronic circuit that implements a wireless protocol, e.g., Wi-Fi, that enables network device 1140 to communicate through a wireless network extending beyond a single hydroponic system. The wireless network may include a local network for a facility containing one or more hydroponic systems and may connect to a wide area network or the Internet, allowing network device 1140 to communicate with remote or cloud-based devices and systems.

Figure 13:
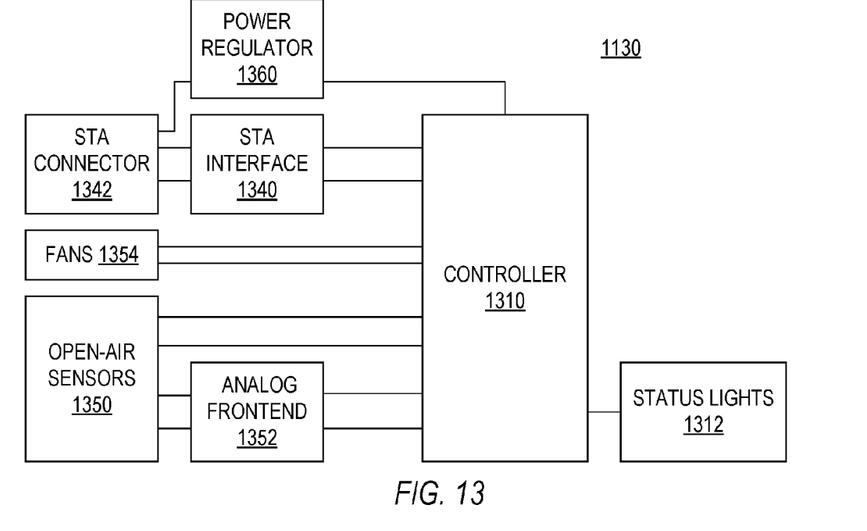
FIG. 13 is a block diagram of an implementation of an air sensor electronics module.

FIG. 13 is a block diagram of one implementation of an air sensing electronics (ASE) module 1130. ASE module 1130 includes a controller 1310 that may be programmable to operate open-air sensors 1350, receive measurements from sensors 1350, and transmit the measurements to network station 1140. In the illustrated implementation, sensors 1350 may be able to digitally communicate with controller 1310 or may provide analog measurement signals to an analog frontend 1352 that converts the analog signals to digital signals suitable for controller 1310. Sensors 1350 may include a variety of sensors including but not limited to one or more light sensors, temperature sensors, or gas sensor such as oxygen, carbon dioxide, or carbon monoxide sensors. Controller 1310 may operate one or more fans to circulate air for measurement by the gas sensors among open-air sensors 1350. Controller 1310 may communicate information such as sensor measurements to network station 1140 through an interface circuit 1340 such as an RS-485 compliant interface chip connected to network station 1140 through a connector 1242, e.g., an RJ-45 connector, and a cable not shown. Alternatively, interface 1340 may implement a local wireless connection between ASE module 1130 and network station 1140. A power regulator 1360 is used in the implementation of FIG. 13 to receive power through connector 1324, e.g., from network station 1140, and to supply regulated power in ASE module 1130.

Figure 14:
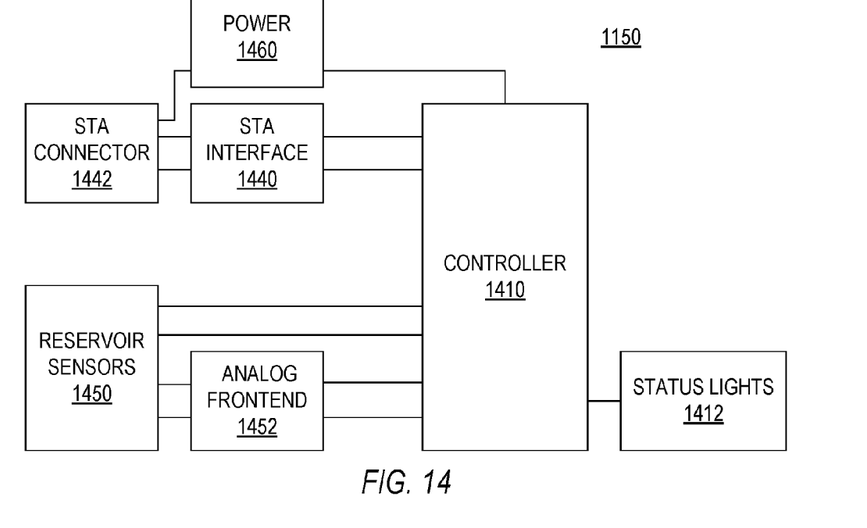
FIG. 14 is a block diagram of an implementation of a water sensor electronics module.

FIG. 14 is a block diagram of one implementation of a water sensing electronics (WSE) module 1150. WSE module 1150 includes a controller 1410 that may be programmable to operate reservoir sensors 1450, receive measurements from sensors 1450, and transmit the measurements to network station 1140. In the illustrated implementation, sensors 1450 may be able to digitally communicate directly with controller 1410 or able to provide analog measurement signals to an analog frontend 1452 that converts the analog signals to digital signals suitable for controller 1410. Sensors 1450 may include a variety of sensors that may be used in the reservoir of a hydroponic system. Sensors 1450 may include, for example, a level sensor to measure the amount of the nutrient solution in the reservoir, a temperature sensor to measure the temperature of the nutrient solution, a pH sensor, and a set of chemical sensors to measure the chemical composition of the nutrient solution. Controller 1410 may communicate information such as sensor measurements to network station 1140 through an interface circuit 1440 such as an RS-485 compliant interface chip connect to network station 1140 through a connector 1442, e.g., an RJ-45 connector, and wire or cables not shown. Alternatively, interface 1440 may implement a local wireless connection from WSE module 1150 to network station 1140. A power system 1460 in the implementation of FIG. 14 may be a power regulator circuit that receives electrical power, e.g., from network station 1140, through connector 1442 and supplies regulated power in WSE module 1150. Alternatively, power circuit 1460 may be a battery system that provides power in WSE module 1150 and particularly powers sensors 1450, which may operate in the wet environment inside the reservoir of a hydroponic system. Use of a battery may reduce electrical damage and shock risks when compared to powering WSE module 1150 using the main power supply of the hydroponic system. In yet another embodiment, power circuit 1460 may use an inductive coupling and a power receiving circuit that may inductively receive power from the hydroponic system.

Although particular implementations have been disclosed, these implementations are only examples and should not be taken as limitations. Various adaptations and combinations of features of the implementations disclosed are within the scope of the following claims.

What is claimed is:
1. A sensing system comprising:
a first sensor system configured to measure a plurality of characteristics of an environment surrounding a plant in a hydroponic system;
a network device including a controller, a first communication interface configured for communication with the first sensor system, and a network interface configured for communication through a network, the network device being configured to transmit measurements from the first sensor system through the network to a remote device;
a housing containing the first sensor system and the network device, wherein a portion of the housing has a shape that matches a collar in the hydroponic system and that allows the sensing system to be inserted into or removed from the collar; and
a power receiving circuit in the housing, wherein:
inserting the housing in the collar positions the power receiving circuit for an inductive coupling with a power transmitting circuit in the collar; and
the power receiving circuit uses an induce voltage to supply power to the second sensor system.
2. The system of claim 1, further comprising:
a second sensor system that measures a plurality of characteristics of a nutrient solution in a reservoir of the hydroponic system, wherein
the network device further includes a second communication interface configured for communication with the second sensor system, the network device being further configured to transmit measurements from the second sensor system through the network to the remote device.

3. The system of claim 2, wherein the network device further comprises a third communication interface configured for communication with control electronics of the hydroponic system.

4. The system of claim 2, wherein the second sensor system includes a sensor selected from a group consisting of temperature sensors, pH sensors, electrical conductivity sensors, total dissolved solids sensors, dissolved oxygen sensors, total suspended solids sensors, sensors specific chemicals or nutrients, and reservoir level sensors.

5. The system of claim 4, wherein the first sensor system includes a sensor selected from a group consisting of a light intensity sensor, a spectrometer, an air velocity sensor, an oxygen sensor, a carbon dioxide sensor, and a carbon monoxide sensor.

6. The system of claim 2, wherein the housing further contains the second sensor system.

7. The system of claim 6, wherein inserting the housing into the collar positions a portion of the second sensor system in the nutrient solution and positions a portion of the first sensor system adjacent to a plant fixture of the hydroponic system.

8. The system of claim 1, wherein the first communication interface implements wireless communications between the network device and the first sensor system.

9. The system of claim 1, wherein the first sensor system includes a sensor selected from a group consisting of a light intensity sensor, a spectrometer, an air velocity sensor, an oxygen sensor, a carbon dioxide sensor, and a carbon monoxide sensor.

10. The system of claim 1, wherein the network interface is configured for communication through a wireless network.

11. A sensing system for hydroponics, the system comprising:
a sensor system that measures a plurality of characteristics of a nutrient solution in a reservoir of a hydroponic system;
a network device including a controller, a first communication interface configured for communication with the sensor system, and a network interface configured for communication through a network, the network device being configured to transmit measurements from the sensor system through the network to a remote device;
a housing containing the sensor system and the network device, wherein a portion of the housing has a shape that matches a collar in the hydroponic system and that allows the sensing system to be inserted into or removed from the collar; and
a power receiving circuit in the housing, wherein:
inserting the housing, in the collar of the hydroponic system positions the power receiving circuit for an inductive coupling with a power transmitting circuit in the collar; and
the power receiving circuit uses an induce voltage to supply power to the sensor system.

12. The system of claim 11, wherein the sensor system includes a sensor selected from a group consisting of temperature sensors, pH sensors, electrical conductivity sensors, total dissolved solids sensors, dissolved oxygen sensors, total suspended solids sensors, sensors specific chemicals or nutrients, and reservoir level sensors.

13. The system of claim 11, wherein inserting the housing into the collar places a portion of the sensor system in the nutrient solution.

14. The system of claim 11, wherein the network device further comprises a second communication interface configured for communication with control electronics of the hydroponic system.

15. The system of claim 11, wherein the first communication interface implements wireless communications between the network device and the sensor system.

16. The system of claim 11, wherein the network interface is configured for communication through a wireless network.

17. A hydroponic system comprising:
a plant fixture;
a reservoir configured to contain a nutrient solution for growing of a plant in the plant fixture;
control electronics for the hydroponic system;
a first sensor system that measures a plurality of characteristics of the nutrient solution;
a second sensor system that measures a plurality of characteristics of an environment surrounding the plant; and
a network device including a controller, a first communication interface configured for communication with the first sensor system, a second communication interface configured for communication with the second sensor system, a third communication interface configured for communication with the control electronics; and a network interface configured for communication through a wireless network, the network device being configured to transmit measurements from the first and second sensor systems through the wireless network to a remote device and through the third communication interface to the control electronics;
a collar;
a power transmission circuit in the collar;
a power receiving circuit; and
a housing containing the second sensor system, the network device, and the power receiving circuit, wherein a portion of the housing has a shape that matches the collar and that allows the housing to be
inserted into or removed from of the collar.

18. The system of claim 17, wherein the system further comprises:
a first H-field communications circuit in the collar; and
a second H-field communications circuit in the housing, wherein the control electronics communicates with the network device through an inductive coupling between the first H-field communications circuit and the second H-field communications circuit.

* * * * *